United States Patent [19]

Hostetler

[11] Patent Number: 5,756,116
[45] Date of Patent: May 26, 1998

[54] NUCLEOSIDE PHOSPHATE THERAPY FOR VIRAL INFECTION

[76] Inventor: Karl Y. Hostetler, 14024 Rue St. Raphael, Del Mar, Calif. 92014

[21] Appl. No.: 758,501

[22] Filed: Dec. 2, 1996

Related U.S. Application Data

[63] Continuation of Ser. No. 60,258, May 12, 1993, Pat. No. 5,580,571, which is a continuation of Ser. No. 777,683, Oct. 15, 1991, abandoned.

[51] Int. Cl.$^6$ .............................. A61K 9/70; A61K 31/74; A61K 31/52; A01N 43/90
[52] U.S. Cl. ................ 424/443; 424/78.02; 424/78.07; 424/405; 514/262; 514/265; 514/266; 514/357; 514/931; 514/934; 514/969; 546/331
[58] Field of Search .................................. 424/405, 443, 424/78.02, 78.07; 514/262, 263, 265, 357, 931, 934, 969; 546/331

[56] References Cited

U.S. PATENT DOCUMENTS

| | | |
|---|---|---|
| 4,146,715 | 3/1979 | Schaeffer . |
| 4,199,574 | 4/1980 | Schaeffer . |
| 4,294,831 | 10/1981 | Schaeffer . |
| 4,323,573 | 4/1982 | Schaeffer . |
| 4,360,522 | 11/1982 | Schaeffer . |
| 4,634,719 | 1/1987 | Takaishi et al. . |
| 4,758,572 | 7/1988 | Spector et al. . |
| 4,897,394 | 1/1990 | Zimmerman et al. . |
| 5,021,437 | 6/1991 | Blumenkopf . |
| 5,223,263 | 6/1993 | Hostetler et al. . |
| 5,274,162 | 12/1993 | Glazier . |

FOREIGN PATENT DOCUMENTS

| | | |
|---|---|---|
| 0350287 | 7/1989 | European Pat. Off. . |
| 1590500 | 6/1981 | United Kingdom . |
| 2168350 | 6/1986 | United Kingdom . |
| 9119721 | 12/1991 | WIPO . |

OTHER PUBLICATIONS

Agranoff, B. et al. (1963) Cytidine Diphosphatase—dl—Dipalmitin. Biochem. Prep. 10:47–51.

Ellis, M. et al. (1989) Orofacial infection of athymic mice with defined mixtures of acyclovir–susceptible and acyclovir–resistant herpes simplex virus type 1. Antimicrobial Agents and Chemotherapy 33(3):304–310.

Furman, P. et al., (1979) Inhibition of herpes simplex virus–induced DNA polymerase activity and viral DNA replication by 9–(2–hydroxyethoxymethyl)guanine and its triphosphate. J. Virol. 32:72–77.

Fyfe, J. et al. (1978) Thymidine kinase from herpes simplex virus phosphorylates the new antiviral compound, 9–(2–hydroxyethoxymethyl)guanine. J. Biol. Chem. 253:8721–8727.

Gomex–almaguer, D. et al. (1988) Acyclovir in the treatment of aplastic anemia. Amer. J. of Hematology 29:172–173.

King (1988) History, pharmacokinetics, and pharmacology of acyclover. J. Am. Acad. Dermatol. 18:176–179 (Abstract only).

Krenitsky, T. et al. (1990) Nucleotide analogue inhibitors of purine nucleoside phosphorylase. The Journal of Biological Chemistry 265(6):3066–3069.

Lobe, D. et al. (1991) Synergistic topical therapy by acyclovir and A110U for herpes simplex virus induced zosteriform rash in mice. Antiviral Research 15:87–100.

Masch et al. (1965) Nivea, the Prototype of Lanolin Absorption Creams. A history of Nivea Cream. American Perfumer and Cosmetics 80:35–38.

Merta et al. (1990) Inhibition of herpes simplex virus DNA polymerase by diphosphates of acyclic phosphonylmethoxyalkyl nucleotide analogues. Antiviral Research 13:209–218.

O'Brien, W. et al. (1990) Nucleoside metabolism in herpes simplex virus–infected cells following treatment with interferon and acyclovir, a possible mechanism of synergistic antiviral activity. Antimicrob. Agents and Chemother. 34(6):1178–1182.

Ott, D.G. et al. (1967) Chemical synthesis of nucleoside triphosphates. Anal. Biochem. 21:469–472.

Remington's Pharmaceutical Sciences, 15th Edition., 175. Mack Publishing Company., Easton, Pennsylvania 18042. (Chapter 87: Blaug, Seymour).

Rune, S.J. et al. (1990) Acyclovir in the prevention of duodenal ulcer recurrence. Gut 31:151–152.

Spruance, S. et al. (1982) Treatment of herpes simplex labialis with topical acyclovir in polyethylene glycol. J. Infect. Dis. 146:85–90.

Spruance, S. et al. (1984) Early patient–initiated treatment of herpes labialis with topical 10% acyclovir. Antimicrob. Agents Chemother. 25:553–555.

Straus, S. (1989) Effect of oral acyclovir treatment on symptomatic and asymptomatic virus shedding in recurrent genital herpes. Sexually Transmitted Diseases 16(2):107–113.

Toorchen, D. et al. (1983) Mechanisms of chemical mutagenesis and carcinogenesis: effects on DNA replication of methylation at the 06–guanine position of dGTP. Carcinogenesis 4:1591–1597.

Welch, C.J. et al. (1985) The chemical synthesis and antiviral properties of an acyclovir–phospholipid conjugate. Acta Chemica Scandinavica B39:47–54.

Whitley, R. et al. (1990) Immunobiology and Prophylaxis of Human Herpesvirus Infections, C. Lopex (ed), Plenum Press, New York pp. 243–253.

Yoshikawa, M. et al. (1969) Phosphorylation. III. Selective phosphorylation of unprotected nucleosides. Bull. Chem. Soc. Japan 42:3505–3508.

Yoshikawa, et al. (1967) A novel method for phosphorylation of nucleosides to 5'–nucleotides. Tetrahedron Lett., 50:5065–5068.

Leibman, K., et al. (1955) The metabolism of $P^{32}$–labeled ribonucleotides in tissue slices and cell suspensions. J. Bio. Chem. 216:823–830.

Glazier, A., et al. The metabolism and antiviral activity of a novel group of anti–herpes prodrugs. Paper No. 90, presented at The Ninth International Conference on Antiviral Research, Uribandai, Fukushima, Japan, May 23, 1996.

*Primary Examiner*—Carlos A. Azpuru
*Attorney, Agent, or Firm*—Knobbe, Martens, Olson & Bear LLP

[57] ABSTRACT

Compositions for topical use in herpes virus infections comprising anti-herpes nucleoside analogue phosphate esters, such as acyclovir monophosphate and acyclovir diphosphate, which show increased activity against native strains of herpes virus as well as against resistant strains, particularly thymidine kinase negative strains of virus. Also disclosed are methods for using the topical compositions in treatment of herpes disease.

10 Claims, 3 Drawing Sheets

1

NUCLEOSIDE PHOSPHATE THERAPY FOR VIRAL INFECTION

This application is a continuation of U.S. patent application Ser. No. 08/060,258, filed May 12, 1993, now U.S. Pat. No. 5,580,571, which is a continuation of U.S. patent application Ser. No. 07/777,683, filed Oct. 15, 1991, now abandoned.

BACKGROUND OF THE INVENTION

1. Field of the Invention

The present invention relates to the topical treatment of cutaneous virus infections. It relates particularly to the topical treatment of herpes simplex infections, including herpes simplex types 1 and 2, using formulations comprising phosphate esters of anti-herpes antiviral nucleoside analogues such as acyclovir.

2. Background of the Art

Acyclovir (ACV) is an antiviral nucleoside analogue of guanosine which contains an unusual incomplete (acyclic) sugar moiety. Nucleoside analogues interrupt the process of DNA replication in cells, and are for that reason useful as antiviral and antineoplastic agents. ACV is particularly effective in treating herpes simplex virus infections of types I and II. The antiherpes virus activity of ACV in cells occurs with low toxicity because ACV is selectively phosphorylated by HSV thymidine kinase, but not host cell thymidine kinase. As a consequence, only cells infected with HSV can form ACV monophosphate (ACV-MP). ACV-MP is then anabolically converted by cellular enzymes to ACV triphosphate, the active agent that interferes with viral replication. (Fyfe, J., et al., *J. Biol. Chem.* 253:8721–8727 (1978); Furman, P., et al., *J. Virol.* 32:72–77 (1979)).

The anti-herpes virus activity of acyclovir has been demonstrated in inhibiting the replication of herpes simplex virus in tissue culture cells (O'Brien, W., et al., *Antimicrob. Agents and Chemother.* 34:1178–1182 (1990); it has also been demonstrated in clinical studies wherein patients infected with HSV were treated with orally administered ACV (Whitley, R., *Immunobiol. and Prophylaxis of Human Herpesvirus Infections*, C. Lopez et al, (eds) Plenum Press, NY 1990; and Straus, S., *Sexually Transmitted Diseases* 16(2):107–113 (1989).

Acyclovir is the treatment of choice for mucosal and cutaneous HSV infections, although, patients receiving topical acyclovir therapy experience some reductions of their symptoms, healing is slow and incomplete (Spruance, S., et al., *J. Infect. Dis.* 146:85–90 (1982); and Spruance, S., et al., *Antimicrob. Agents Chemother.* 25:553–555 (1984).

Combination treatment using ACV together with interferon for herpes virus infected cultured cells (O'Brien, W., et al., *Antimicrob. Agents and Chemother.* 34(6):1178–1182 (1990) or using ACV together with A1110U, an HSV inactivator, as a topical therapy for herpetic keratitis in athymic mice (Lobe, D., et al., *Antiviral Research* 15:87–100 (1991) showed synergistic antiherpesvirus I activity over the use of ACV alone.

Acyclovir has been used with qualified success in a clinical trial to treat another viral disease, varicella (chickenpox) (Whitley, R., et al., *Immunobiology and Prophylaxis of Human Herpesvirus Infections,* C. Lopez (ed), Plenum Press, New York (1990) pp. 243–253. It has also been used experimentally but without success in treating other disorders in which a viral etiology was hypothesized, such as aplastic anemia (Gomez-Almaguer, D., et al. *Amer. J. of Hematology* 29:172–173 (1988) and duodenal ulcer (Rune, S. J., et al., *Gut* 31:151–152 (1990)).

Acyclovir phosphates have been shown to be efficacious against wild type or laboratory isolates of HSV-1 infected cultured cells in vitro, but have little or no efficacy against thymidine kinase defective mutants of HSV under the same conditions. (See data of FIGS. 1 and 2).

In immunosuppressed patients, such as those with HIV (AIDS) infections or transplant recipients who are taking immunosuppressive drugs to prevent transplant rejection, ACV has been given chronically to prevent troublesome outbreaks of herpes. Such therapy provides a selective pressure which leads to mutations in HSV thymidine kinase (90% frequency) as well as DNA polymerase (10% frequency), which in turn results in ACV-resistant viral strains. There is no effective topical therapy for these acyclovir resistant herpes virus strains.

SUMMARY OF THE INVENTION

According to the invention, there are provided acyclovir phosphate esters and other antiherpes antiviral nucleoside analogue phosphate esters that are effective in the treatment of mucosal and cutaneous herpetic lesions due to herpes virus infections. These agents surprisingly show antiviral activity against lesions due to thymidine kinase defective herpes virus infections, even though they are relatively inactive against these mutant viruses in cultured cells. The invention also provides pharmaceutical formulations, comprising an effective, antiviral concentration of an acyclovir derivative which can be acyclovir monophosphate, acyclovir diphosphate, acyclovir monophosphate glycerol, acyclovir diphosphate glycerol, acyclovir monophosphate morphòlidate, acyclovir monophosphate glycerol, acyclovir diphosphate glycerol, acyclovir monophosphate isopropylidene glycerol, acyclovir diphosphate isopropylidene glycerol, or a mixture thereof, in a pharmaceutical carrier suitable for topical use.

Other antiherpes simplex nucleosides which rely on phosphorylation by viral thymidine kinase will also exhibit enhanced activity when applied to the skin of infected patients as their phosphate esters in a suitable topical formulation.

According to another aspect of the invention, there is provided a method for the topical treatment of a viral infection, comprising applying a formulation comprising any of the acyclovir phosphate derivatives of the invention, or a mixture thereof, to the mucosal or cutaneous lesions of a virus infected animal, including a human or other mammal. In a preferred embodiment of the method, the animal is infected with a herpes virus. In a particularly preferred embodiment, the animal is infected with a herpes virus strain that is resistant to acyclovir. The acyclovir resistant herpes virus strain can be a viral strain in which resistance to the antiviral agent is due to an alteration or defect in the thymidine kinase gene.

In accordance with another aspect of the present invention, an anti-herpes nucleoside analogue monophosphate is used in the preparation of a medicament for the treatment of a mucosal or cutaneous viral infection. In a preferred embodiment, the nucleoside monophosphate is a water soluble salt. In another preferred embodiment, the viral infection is herpes simplex virus, type 1 or type 2.

In another aspect of the present invention, the anti-herpes nucleoside analogue monophosphate is used together with a pharmaceutically acceptable carrier in the preparation of a medicament for the treatment of a mucosal or cutaneous viral infection. In a preferred respect, the pharmaceutically acceptable carrier is selected from the group consisting of an aqueous cream and polyethylene glycol.

DETAILED DESCRIPTION OF THE INVENTION

Figure 1:
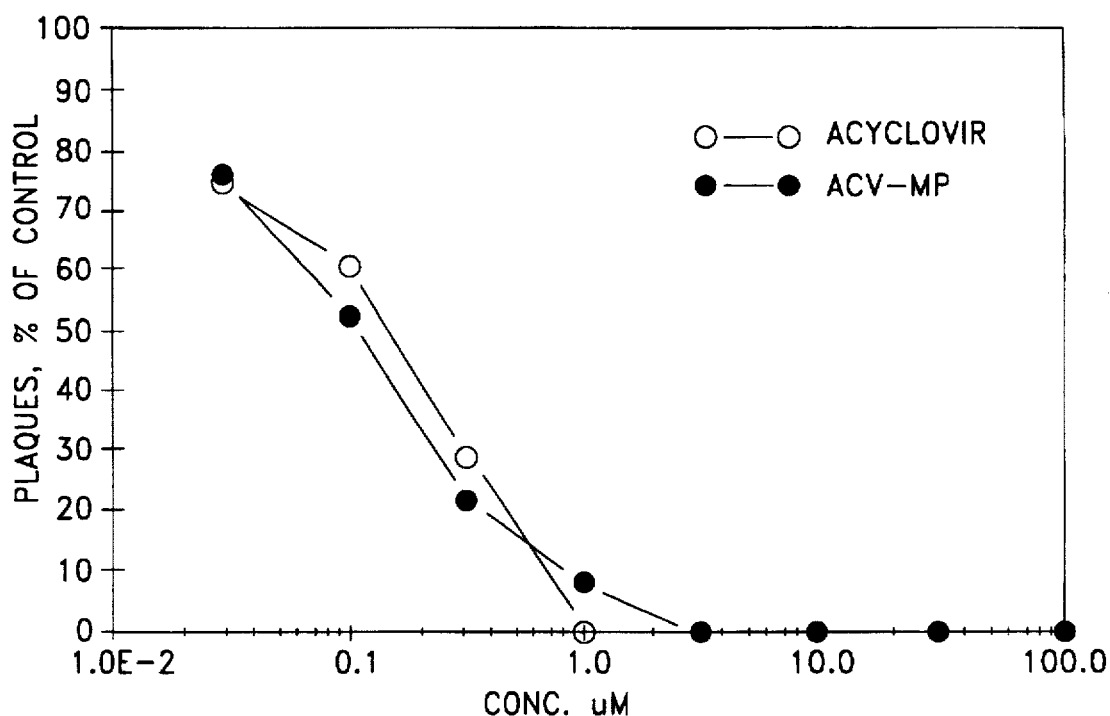
FIG. 1 illustrates the comparative effect of acyclovir and acyclovir monophosphate on herpes simplex virus replication in Wi38 fibroblasts.

The present invention provides acyclovir phosphate derivatives that demonstrate excellent topical activity against herpes simplex virus (HSV) infections, particularly against ACV-resistant mutants of HSV.

Acyclovir is an analogue of the purine base, guanine, having a substituent group at the 9-position, and having an acyclic sugar group from which the common name is derived. The chemical name of acyclovir is 9-(2-hydroxyethoxymethyl)-guanine, which has the structure:

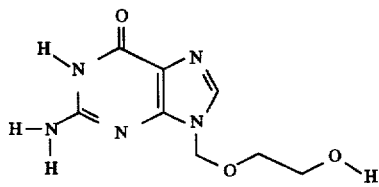

The acyclovir phosphate derivatives of the invention have a substituent, R, at the terminal O-locant of the acyclic sugar group, as follows:

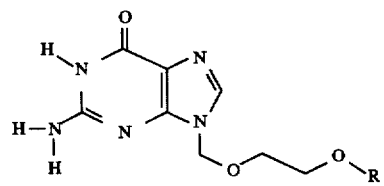

wherein the R substituents are as follows:

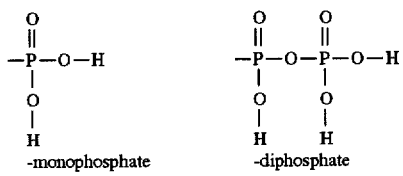
-monophosphate    -diphosphate

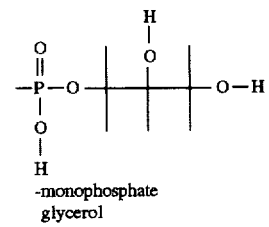
-monophosphate glycerol

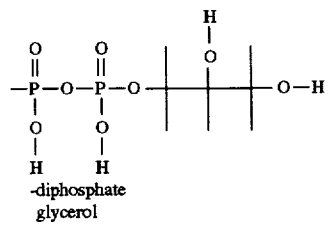
-diphosphate glycerol

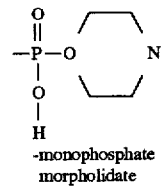
-monophosphate morpholidate

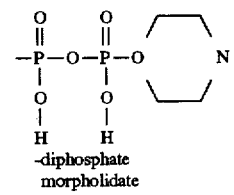
-diphosphate morpholidate

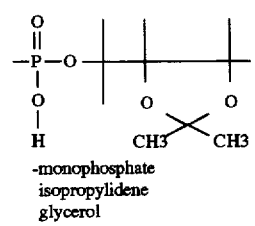
-monophosphate isopropylidene glycerol

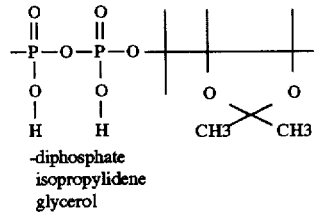
-diphosphate isopropylidene glycerol

According to the invention, acyclovir monophosphate (ACV-MP), acyclovir diphosphate (ACV-DP), acyclovir monophosphate glycerol (ACV-MP-G), acyclovir diphosphate glycerol (ACV-DP-G), acyclovir monophosphate morpholidate (ACV-MP-morpholine), acyclovir monophosphate isopropylidene glycerol (ACV-MP-isoP-G), or acyclovir diphosphate isopropylidene glycerol (ACV-DP-isoP-G), either alone or combined, are prepared in a suitable topical pharmaceutical formulation and applied to the cutaneous lesions of an HSV-infected individual. The compounds ACV-MP, ACV-DP, ACV-DP-G, the morpholine derivative of acyclovir, and the acyclovir isopropylidene glycerol derivatives described, are non-lipid, water soluble phosphate esters, and are therefore preferably provided in an aqueous base topical formulation.

Surprisingly, we have discovered that the monophosphates of acyclovir, and we expect that monophosphate derivatives of other nucleosides will, exhibit enhanced topical anti-HSV activity. We have also demonstrated that salts of monophosphate derivatives nucleosides can be easily prepared, and that such salts exhibit enhanced solubility in aqueous media, i.e., cream, gels, or other aqueous dispersions. Moreover, such salts are soluble in polyethylene glycol media which provides a unique mucosal or cutaneous dispersion.

Similarly, monophosphates, diphosphates, and other phosphate esters of other antiherpes simplex nucleosides will exhibit enhanced topical activity as those above noted. The following herpes antiviral nucleosides exhibit enhanced activity as phosphate esters:

1-beta-D-arabinofuranosyl-E-5-(2-bromovinyl)uracil [broavir; BV-araU];

2'-fluorocarbocyclic-2'-deoxyguanosine;

6'-fluorocarbocyclic-2'-deoxyguanosine;

1-(beta-D-arabinofuranosyl)-5(E)-(2-iodovinyl)uracil;

SQ 34,514;

HOE 602;

triflurothymidine;

9-[(1,3-dihydroxy-2-propoxy)methyl]guanine;

5-ethyl-2'-deoxyuridine;

E-5-(2-bromovinyl)-2'-deoxyuridine;

5-(2-chloroethyl)-2'-deoxyuridine;

1-(2-deoxy-2-fluoro-beta-D-arabinofuranosyl)-5-iodocytosine (FIAC);

1-(2-deoxy-2-fluoro-beta-D-arabinofuranosyl)-5-iodouridine (FIAU);

buciclovir;

6-deoxyacyclovir;

9-(4-hydroxy-3-hydroxymethylbut-1-yl)guanine;

E-5-(2-iodovinyl)-2'-deoxyuridine;

5-vinyl-1-beta-D-arabinofuranosyluracil (V-araU);

1-beta-D-arabinofuranosulthymine (Ara-T);

2'-nor-2'deoxyguanosine (2'NDG);

9-(4-hydroxy-3-hydroxymethylbut-1-yl) guanine (penciclovir, BRL 3912)

1-beta-D-arabinofuranosyladenine (Ara-A; vidarabine)

The various phosphate esters of these compounds may be prepared essentially as described below for acyclovir.

SYNTHESIS OF ACYCLOVIR PHOSPHATE ESTERS

The present invention provides methods for the synthesis of acyclovir mono- and diphosphates, acyclovir monophosphate morpholidates, acyclovir mono- and diphosphate glycerols, and acyclovir mono- and diphosphate 1,2-isopropylidene glycerol.

Acyclovir monophosphate can be prepared from acyclovir according to the method of Yoshikawa, M., et al., *Bull. Chem. Soc. Japan* 42:3505–3508 (1969) as modified by the method of Toorchen, D. and Topal, M., *Carcinogenesis* 4:1591–1597 (1983), and exemplified in Example 1. Acyclovir diphosphate can be prepared, in the manner of other nucleoside analogues, by the method of Ott, D. G., et al., *Anal. Biochem.* 21:469–472 (1967), using either tributylammonium phosphate or tributylammonium pyrophosphate as the phosphate donor.

Methods for the preparation of acyclovir diphosphate glycerol are presented in Examples 2 through 4. In general, the nucleoside phosphate glycerols are prepared in a manner similar to that for the preparation of phosphatidyl nucleosides. In the approach described in Example 3, acyclovir phosphate is activated by the addition of a leaving group, for example, morpholine, according to Example 2, and condensed with glycerol-3-phosphate dicyclohexylammonium salt in the presence of N,N'-dicyclohexylcarbodiimide (DCC). Alternatively, as described in Example 4, glycerol phosphate, having the reactive hydroxyl groups protected by an isopropylidene moiety, is activated by addition of morpholidate, and then condensed with acyclovir monophosphate under the conditions described for Example 2.

A number of acyclovir-diphosphate-diglycerides (ACV-DP-DG) containing various acyl chains have been prepared in the past by the condensation of the appropriate diacylphosphatidic acid morpholidate (PA-Morpholidate) and acyclovir monophosphate (ACV-MP.) A method by which the procedure can be carried out is described by Agranoff, B. and Suomi, W., *Biochem. Prep.* 10:47–51 (1963). Alternatively, the morpholidate of the nucleoside monophosphate is prepared and condensed with a phosphatidic acid as described in U.S. patent application Ser. No. 07/706, 873 entitled "Liponucleotide Synthesis," and by Hong, et al., British Patent Application No. 2,168,350.

The chemical methods above are generally disclosed in terms of their general application to the preparation of compounds of the invention. Occasionally, the reaction may not be applicable as described to each compound included within the disclosed scope. The compounds for which this occurs will be readily recognized by those skilled in the art. In all such cases, either the reactions can be successfully performed by conventional modifications known to those skilled in the art, e.g. by appropriate protection of interfering groups, by changing to alternative conventional reagents, or by routine modification of reaction conditions. Alternatively, other reactions disclosed herein or otherwise conventional will be applicable to the preparation of the corresponding compounds of the invention. In all preparative methods, all starting materials are known or readily preparable from known starting materials. Unless otherwise indicated, all parts and percentages are by weight.

Figure 2:
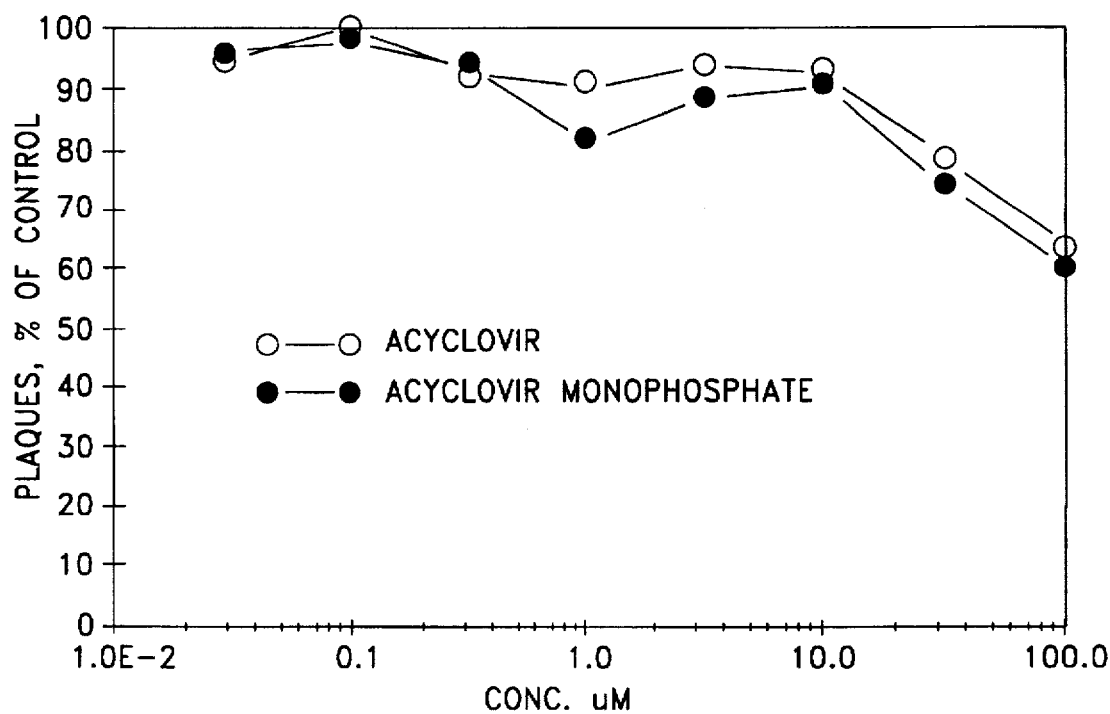
FIG. 2 illustrates the comparative effect of acyclovir and acyclovir monophosphate on the replication of HSV-DM.21 TK mutant in vitro.

The acyclovir derivatives of the invention, comprising ACV-MP, ACV-DP, ACV-MP-glycerol, ACV-DP-glycerol, ACV-MP-isopropylidene glycerol, and ACV-DP isopropylidene glycerol were found to have particular efficacy in topically treating the herpetic lesions of acyclovir-resistant HSV-1 infections. Example 7 demonstrates that infection of cultured cells with wild type isolates and laboratory strains of HSV can be treated with equal success using acyclovir, acyclovir monophosphate (Example 7; FIG. 1). For these viral infections in Wi38 fibroblasts, both acyclovir and acyclovir monophosphate have the same $IC_{50}$ of about 1 or 2 µM concentration. However, when the same cultured cell system is infected with an acyclovir-resistant strain of virus, HSV-DM.21, lacking the thymidine kinase necessary to convert acyclovir to acyclovir monophosphate, acyclovir and acyclovir monophosphate are ineffective in reducing the number of viral plaques (Example 7; FIG. 2).

Figure 3:
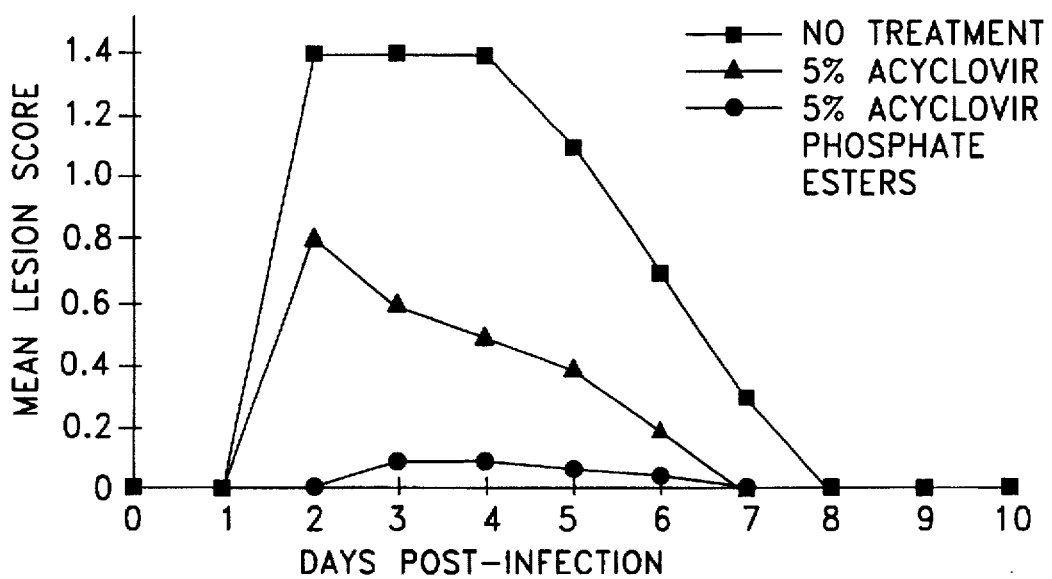
FIG. 3 illustrates the comparative effect of topical acyclovir and acyclovir phosphate esters on acyclovir-resistant HSV-1 infections of the TK-deficient type in HRS/J mice.
Figure 4:
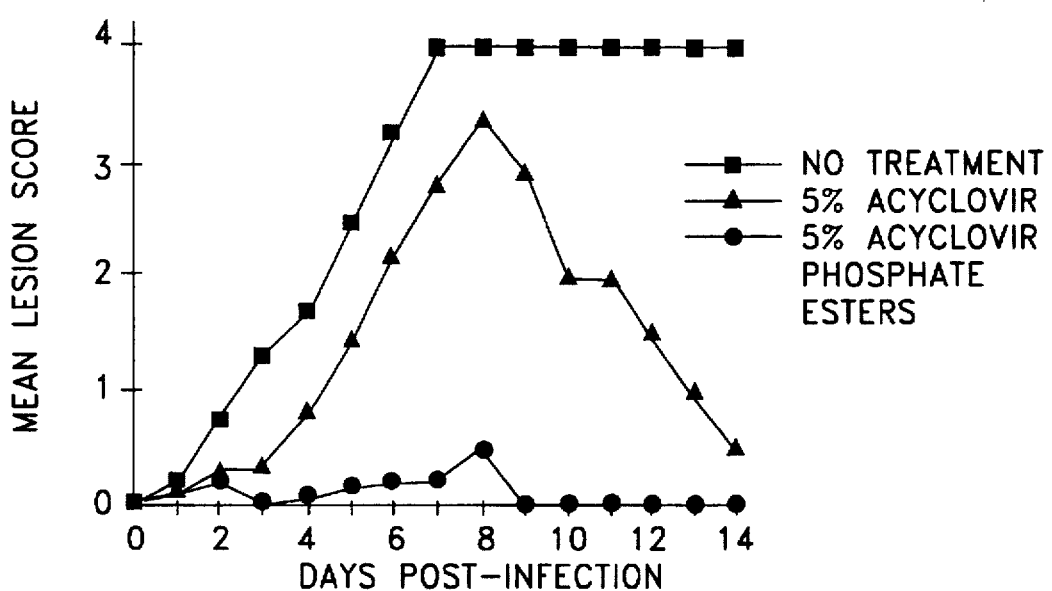
FIG. 4 illustrates the comparative effect of topical acyclovir and acyclovir phosphate esters on acyclovir-resistant HSV-1 infections of the TK-altered type in HRS/J mice.

The efficacy of acyclovir phosphate esters with respect to acyclovir-resistant cutaneous HSV-1 infections is surprising in view of the cultured cell in vitro data above. Acyclovir phosphate esters applied in an aqueous cream to the herpetic lesions of mice infected with acyclovir-resistant HSV-1 were substantially more effective than native acyclovir in reducing the number of such lesions (Example 9; FIGS. 3 and 4).

Accordingly, in view of these results, it is believed that in vitro incorporation of acyclovir, and acyclovir phosphates, proceed through a different mode of operation than in vivo as a topically applied lotion.

TOPICAL FORMULATIONS OF NUCLEOSIDE ANALOGUE PHOSPHATES

The nucleoside analogue derivatives of the invention as previously described can be prepared for topical use by incorporation into a variety of formulations known to those in the art as useful and convenient for dermatological use. The nucleoside analogue derivatives are water soluble, and accordingly an aqueous solution, water-in-oil emulsion, or an aqueous cream are highly preferred formulations. Water solubility of the acyclovir and other nucleoside monophosphates can be enhanced through the preparation of salts, such as sodium, potassium, ammonium, or hydrogen. In a particularly preferred formulation, the active ingredient is prepared in a polyethylene glycol (PEG) vehicle. Alternatively, the active ingredients can be topically applied in a dry powder formulation, using an insoluble powder, such as starch or talc as a diluent or carrier.

The vehicle is an important component of some topical formulations, because it can be selected to enhance penetration, to prolong the duration of activity, or to meet requirement of the site of application. For example, a formulation for application to the callous parts of the body, such as the palms of the hand or bottoms of the feet, can include a penetration enhancing agent such as dimethylsulfoxide propylene glycol or azone™; a powdery formulation can be selected for application to the intertriginous zones such as the crotch, inner elbow or between the fingers or toes. The formulation can also be made up to contain various organic polymers or other compositions known to those of skill in the art to give sustained release of the active antiviral acyclovir derivatives.

A multitude of appropriate topical formulations can be found in the formulary known to all pharmaceutical chemists: Remington's Pharmaceutical Sciences, 15th Edition, 1975, Mack Publishing Company, Easton, Pa. 18042. (Chapter 87: Blaug, Seymour). These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

The concentration of active ingredient in the topical formulations of the invention can be from about 0.01 gm % to 100 gm %; preferably from about 0.1 gm % to 50 gm %; most preferably from about 1 gm % to about 15 gm %. The formulations can further comprise effective concentrations of other agents which help to promote penetration of the skin and healing, as described in the above-referenced formulary and are well known to those of ordinary skill in the art.

Efficacy of topical formulations containing the active phosphate esters of the invention can be evaluated using conventional testing procedures, known to those of skill in the art. For example, a particularly expeditious procedure is the murine "orofacial model," as described by Ellis, M., et al., *Antimicrobial Agents and Chemotherapy* 33:304–310 (1989). In this test system, the pathogenesis of HSV in mice scarified and inoculated on the snout has been shown to be a reasonable model of the disease cycle of cutaneous HSV infection in the immunocompromised host.

The formulations can be applied to the herpetic lesions of the affected skin repeatedly; for example once, twice, or several times a day, and the treatment can be extended for several days until healing is achieved. The risk of incidence of toxicity and irritation is minimal.

Without further elaboration, it is believed that one skilled in the art can, using the preceding description, utilize the invention to its fullest extent.

The present invention is described below in additional detail using the following examples, but the methods described below are applicable to all methods within the scope of the invention and the invention is not limited to the examples given. The following preferred embodiments are, therefore, to be construed as merely illustrative and not limitative of the remainder of the disclosure in any way whatsoever.

EXAMPLE I

Phosphorylation Of Acyclovir Nucleoside Derivatives

We prepared acyclovir nucleoside derivatives through the following methods. Unprotected acyclovir was reacted with $POCl_3$ in trimethyl phosphate (($CH_3O)_3PO$) was performed essentially as described by Yoshikawa et al. *Tetrahedron Letters* 50:5065–5068 (1967); and Yoshikawa, M., Kato et al. *Bull Chem. Soc. Japan* 42:3205–3208 (1967). To a cooled solution (0° C.) of 2M $POCl_3$ in 300–400 ml trimethyl phosphate, acyclovir (1M) was added dropwise with stirring, the reaction temperature being held constant between 0° and 5° C. The progress of the reaction was monitored by means of HPLC using a Mono Q HR 5/5 anion exchange column (Pharmacia, Uppsala, Sweden). Typically, 5 μl of the reaction mixture was neutralized with aqueous sodium hydroxide (final pH 7) and injected on the column.

Elution was performed as follows: washing with water, elution with 0.1M ammonium carbonate, $NH_4HCO_3$, which elutes the acyclovir monophosphate, followed by a linear gradient of 0.1–0.6M $NH_4HCO_3$ which elutes some higher phosphorylated products. The reaction was mostly completed within 45 to 75 minutes as determined by this method, and the reaction product was hydrolyzed and neutralized with 2 volumes of aqueous sodium hydroxide to final pH of 7.

Purification of the product compound was conducted as described above for the analysis of the reaction mixture. By this method, 0.8 moles of acyclovir monophosphate were prepared and purified with a Q Sepharose fast flow column using the same elution conditions.

Yields varied between 80% and 96% after repeated lyophilization from water.

TLC analysis (Silica 60/F254 Plates, Merck) showed a single U.V. and Pi positive spot, using the developing system 1-propanol/25% $NH_3/H^2O$ (20:20:3 by volume)

EXAMPLE II

Preparation Of Acyclovir-monophosphomorpholidate

Acyclovir-monophosphate (5 mmol) and morpholine (20 mmol) were suspended in t-butanol (50 ml) and heated under gentle reflux while N,N'-dicyclohexylcarbodiimide (DCC, 20 mmol) dissolved in t-butanol (50 mmol) was added dropwise over a period of 1 hour. The mixture was stirred under reflux for 12 to 36 hours and evaporated to dryness. The residue was triturated with ether and washed by decantation with the same solvent. The product was purified by recrystallization from methanol-ether mixtures.

EXAMPLE III

Preparation Of sn-Glycero-3-diphospho-acyclovir From Acyclovir-monophosphomorpholidate Acyclovir monophosphomorpholidate (2 mmol), prepared as described in Example 2, was dissolved in dry pyridine (20 ml) and evaporated to dryness under vacuum. The process of dissolving the residue in pyridine and evaporation was repeated three additional times to remove traces of water from the compound. Glycerol-3-phosphate di-monocyclohexylammmonium salt (3 mmol) was added to the dried residue and the mixture was dissolved in 20 ml of pyridine and stirred under inert atmosphere at 60° C. for 12–36 hours. The solvent was evaporated under vacuum and the residue was titrated with ether and the resulting solid was purified by ion exchange chromatography over DEAE sephadex column (2.5 cm × 30 cm) using a linear gradient of ammonium bicarbonate (10 mmol to 300 mmol, 500 ml each). Fractions containing pure product (identified by using TLC and analytical HPLC) were pooled and lyophilized to furnish the title compound.

EXAMPLE IV

Preparation Of sn-Glycero-3-diphospho-acyclovir From 1,2-isopropylidene-sn-glycero-3-monophosphomorpholidate A. Preparation Of 1,2-Isopropylidene-sn-glycero-3-phosphate Phosphorous oxychloride (25 mmol) was added dropwise over a period of 30 minutes to a mixture of 1,2-Isopropylidene-glycerol (20 mmol) (Sigma, St. Louis, Mo.) and triethylamine (100 mmol) that was cooled to 0° C. After stirring the mixture at 0° C. for 10 to 90 minutes. Water (1 ml) was added to stop the reaction. The mixture was then dissolved chloroform (500 ml) and washed with water (3×100 ml). The water wash solutions were combined and back extracted with chloroform (50 ml) and lyophilized. The product was used immediately for subsequent reactions without any additional purification.

B. Preparation Of 1,2-isopropylidene-sn-glycero-3-monophosphomorpholidate 1,2-isopropylidene-sn-glycero-3-phosphate, prepared as described in (A), was condensed with morpholine to prepare 1,2-isopropylidene-sn-glycero-3-monophosphomorpholidate, according to the procedure described for the preparation of acyclovir phosphomorpholidate in Example 2.

Reaction of the intermediate compound, 1,2-isopropylidene-sn-glycero-3-monophosphomorpholidate, with acyclovir monophosphate under the conditions described in Example 2, yielded 1, 2-isopropylidene-sn-glycero-3-monophosphomorpholidate.

1, 2-isopropylidene-sn-glycero-3-diphospho-acyclovir (1 mmol) was dissolved in 50 to 90% aqueous acetic acid and stirred at room temperature for a period of 4 to 12 hours and the crude glycero-3-diphospho-acyclovir product was purified as described above.

EXAMPLE V

Preparation Of sn-glycero-3-phospho-acyclovir 1,2-Isopropylidene-sn-glycero-3-phosphate, 1 mM (prepared as in Example 4B), and acyclovir (1 mM), were suspended in dry pyridine (10 ml) and DCC (4 mmol). Dissolved pyridine (4 ml) was added and the mixture stirred at 25° C. to 60° C. for 12 to 72 hours. The solvent was evaporated and the residue was titrated with ether. The crude product was purified by ion exchange chromatography as described in Example 3. The isopropylidene-protecting group was then removed from the product by treating with aqueous acetic acid to furnish the title compound.

Alternatively, the title compound was also prepared by using 2,4,6-triisopropylbenzenesulfonyl chloride (TPS-Cl) as the condensing agent.

EXAMPLE VI

Preparation Of Acyclovir Phosphate Ester Mixture By The Alkaline Hydrolysis Of Acyclovir Diphosphate Dipalmitoylglycerol Acyclovir-diphosphate-dipalmitoylglycerol (1 mmol) was dissolved in chloroform, to which methanolic sodium hydroxide (2.1 mmol) was added. The reaction was carried for 20 to 90 minutes and the progress was monitored by TLC. Upon completion of the reaction, Dowex-50 X-2 (H+) was added to the reaction mixture to adjust the pH to 7. The resin was separated by filtration and the filtrate was lyophilized and the crude product was purified as described in Example 1.

EXAMPLE VII

Absence Of Antiviral Effect Of Acyclovir Monophosphate In Acyclovir-Resistant TK Mutant Strains Of HSV (DM.21)

Separate cultures of Wi-38 fibroblast cells infected with either wild type strains of herpes simplex virus (HSV) or a mutant strain of HSV (DM.21) were individually treated with acyclovir, or acyclovir monophosphate. The DM.21 mutant lacks the thymidine kinase enzyme which usually converts ACV to ACV-MP, and is therefore resistant to acyclovir. The results for HSV-1 are shown in FIG. 1, and those for HSV-DM.21 are shown in FIG. 2. An $IC_{50}$ is that concentration of antiviral agent which inhibits viral plaque formation 50%.

In wild type isolates and laboratory strains of herpes simplex virus (HSV-1), acyclovir and acyclovir monophosphate have $IC_{50}$s of 0.1 μM (FIG. 1). In contrast, both acyclovir and acyclovir monophosphate have $IC_{50}$s in excess of 100 μM against mutant HSV strains in this assay (FIG. 2).

Based on these results in vitro, one would not expect acyclovir monophosphate to exhibit significant activity when administered topically to animals infected with a thymidine kinase defective or other mutant strain of HSV.

EXAMPLE VIII

Antiviral Effect Of Acyclovir Phosphate Esters In Mice Infected With Acyclovir-Resistant Strains Of HSV Mice of the HRS/J type were infected cutaneously using the snout scarification method as described by Ellis, M. et al., *Antimicrobial Agents and Chemotherapy* 33(3):304–310 (1989). Briefly, groups of 10 mice, under light ether anesthesia, were inoculated on the snout by scarification with a 25-gauge needle, followed by 10 seconds of rubbing with a cotton-tipped applicator soaked in diluted virus. The virus used for infection was a TK-deficient strain, referred to in Ellis, M. et al. (TK$^O$). Three hours post-infection, the animals were treated topically, 3 times daily, for 4 days, with formulations of acyclovir or acyclovir phosphates, in a aqueous cream (AC), according to the Ellis reference cited above.

The results are presented in FIG. 3. A formulation comprising 5 gm % acyclovir was active. In contrast, a formulation comprising 5 gm % of a mixture of 80% acyclovir monophosphate together with 20% other acyclovir phosphate esters (acyclovir diphosphate and acyclovir diphosphate glycerol) showed superior activity, with only a few mice developing herpetic lesions. All lesions were healed by day 8 in all groups.

The above procedure was repeated, with treatment continuing for 5 days, using the TK-altered HSV-1 virus (TK$^A$, Ellis, above), a more virulent strain. Unlike the TK$^O$ virus, TK$^A$ is fatal in untreated mice. Treatment with 5 gm percent acyclovir reduced lesion scores moderately, with most animals surviving and improving substantially by day 14. With the same concentration of phosphate esters, however, there was a dramatic improvement in lesion scores, with all lesions resolved after 9 days, and all animals surviving, as shown in FIG. 4.

EXAMPLE IX

Antiviral Effect Of Acyclovir Monophosphate In Mice Infected With An Acyclovir Resistant Wild Type HSV-1

The procedure of Example 8 was repeated using an acyclovir-sensitive, wild type HSV-1 and a formulation having only acyclovir monophosphate (ACV-MP) as the acyclovir derivative. Two creams were formulated, one having ACV-MP present in the aqueous cream at 14.5 millimoles/100 ml and the other having acyclovir present at 22.2 millimoles/100 ml (both 5 gm %, however, because of the addition of the phosphate group the number of moles of acyclovir present in the monophosphate is reduced relative to neat acyclovir).

Figure 5:
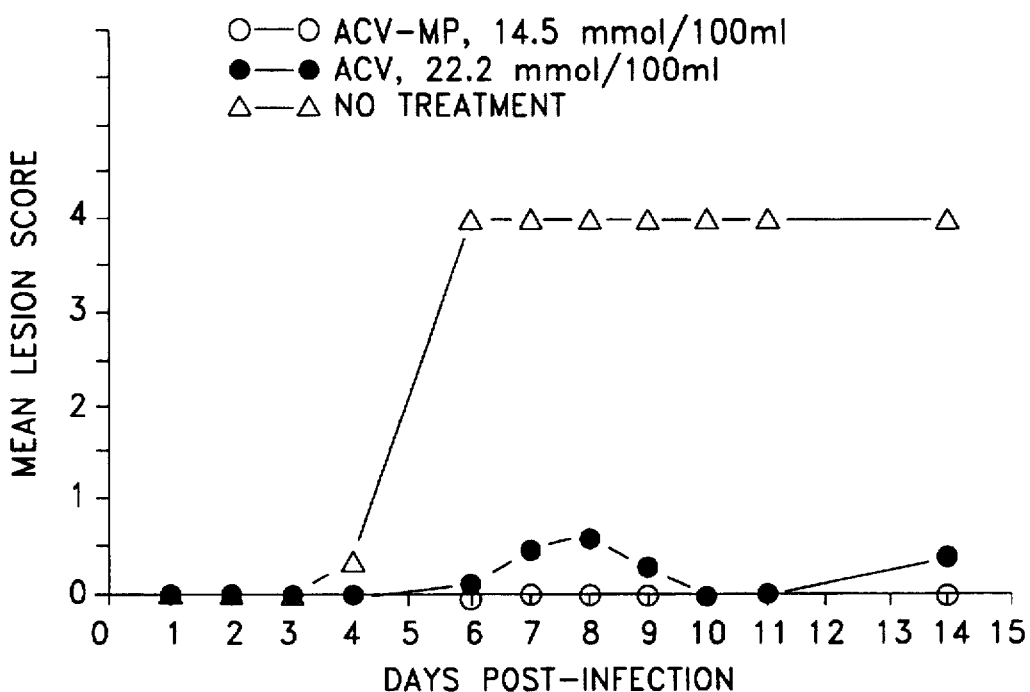
FIG. 5 illustrates the comparative effect of topical acyclovir and acyclovir monophosphate on acyclovir-resistant HSV-1 infections of the wild type in HRS/J mice.

Treatment was initiated 24 hours after infection and continued 4 times daily for four days. The ten untreated mice developed stage 4 lesions by the 5th day and all died by day 14 (FIG. 5). The acyclovir monophosphate-treated animals did not develop lesions and 10 of 10 animals survived (FIG. 5). In the acyclovir-treated group several animals developed mild lesions on days 7-9 which resolved; 9 of 10 ten animals survived.

This study shows that ACV-MP at a lower dosage (14.5 mmol/100 ml) was more effective than acyclovir (22.2 mmol/100 ml) in preventing lesions in wild type HSV-1 infection.

EXAMPLE X

Antiviral Effect Of Acyclovir Monophosphate In Mice Infected With An Acyclovir Resistant RSV-1

Figure 6:
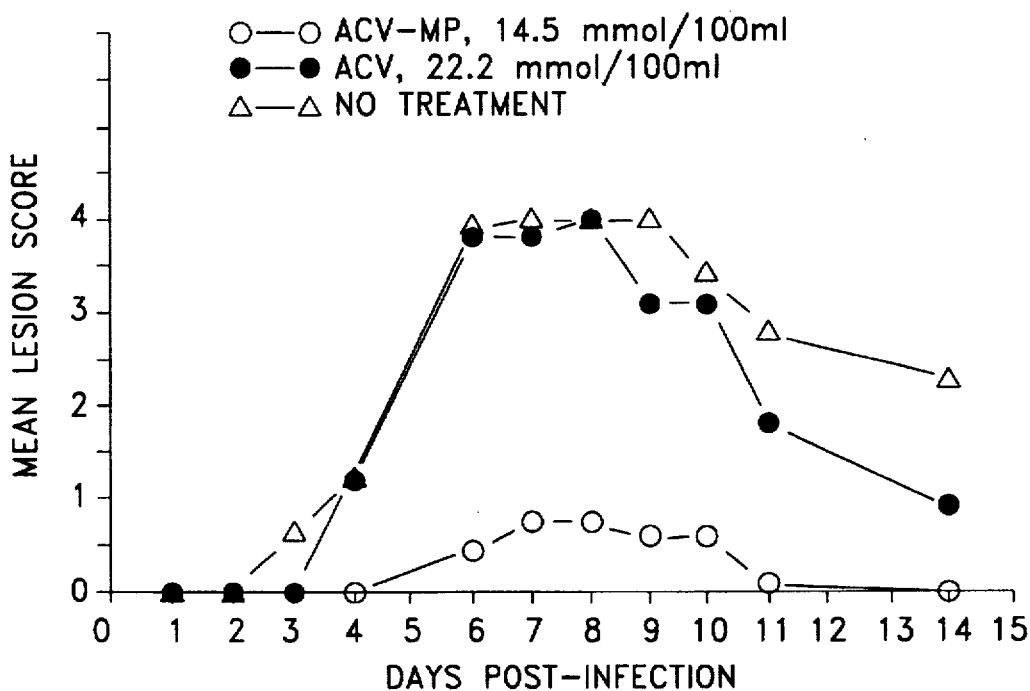
FIG. 6 illustrates the comparative effect of topical acyclovir and acyclovir monophosphate on acyclovir-resistant HSV-1 infections of the TK-altered type in HRS/J mice.

The procedure of Example 8 was repeated using a formulation having only acyclovir monophosphate (ACV-MP) as the acyclovir derivative. Treatment was begun 3 hours post-infection, with treatments occurring twice on the day of infection, and thereafter, three times a day through day 4. Referring now to FIG. 6, ACV-MP at 14.5 mmol/100 ml is clearly more effective than acyclovir at 22.2 mmol/100 ml in reducing lesion scores in animals infected with acyclovir-resistant (TK altered) HSV-1.

In the control and acyclovir-treated groups, 8 of 10 mice survived the 14 day experiment versus 10 of 10 surviving with acyclvoir monophosphate treatment.

EXAMPLE XI

Antiviral Effect Of Acyclovir Monophosphate In Guinea Pigs Infected With An Acyclovir Resistant HSV-2

We tested acyclovir monophosphate (ACV-MP) in aqueous cream (AC) to determine if it was more effective than 5% Acyclovir in polyethylene glycol (ACV-PEG) for treatment of a primary genital herpes. In particular, we studied a genital herpes infection of guinea pigs caused by an ACV-resistant HSV-2. Additionally, we compared acyclovir treatments in two carrier systems: aqueous cream (AC) and polyethylene glycol (PEG). The experiments were placebo-controlled and uninfected animals were treated with each ACV preparation to assess skin and vaginal irritation.

Intravaginal inoculation of weanling guinea pigs with HSV-2 results in a primary genital infection is characterized by initial replication of virus in the vaginal tract followed by the development of external vesicular lesions. Virus titers peak on days one to three in the vaginal tract and gradually clear by days 7-10. The external genital lesions first appear on day four, peak lesion severity occurs on days 6-8, and the lesions generally heal by days 15-18.

Animals were inoculated with the HSV-2 strain 12247, which has an altered thymidine kinase and is resistant to in vitro treatment with ACV. Female Hartley guinea pigs (Charles River, Kingston, N.Y.) weighing 250-300 grams were first vaginally swabbed to remove vaginal secretions. After one hour, the animals were inoculated intravaginally with $2.4 \times 10^4$ plaque forming units (pfu). Inoculation was accomplished by inserting a swab soaked with virus into the vaginal tract and rotating approximately six times.

Groups of 10 guinea pigs were treated both intravaginally and on the external genital skin with 0.1 ml (total of 0.2 ml per animal per treatment) of each preparation. Animals were treated three times daily for seven days beginning 24 hours post-viral inoculation. Three uninfected animals were treated with each preparation on the same schedule to assess local toxicity and irritation.

To determine the efficacy of the various treatments on HSV-2 replication in the vaginal tract, swabs of vaginal secretions were obtained during the primary infection on days 1, 3, 5, 7, and 10 after HSV-2 inoculation. The swabs were placed in tubes containing 2.0 ml of media, vortexed, and frozen at −70° C. until titrated for HSV. When all samples were collected, they were thawed, diluted serially, and HSV-2 titers were determined using rabbit kidney cells in a microtiter CPE assay.

We also measured the development and severity of external genital lesions to determine the efficacy of treatment. Severity of lesions was graded on a 0-5+ score. The presence or absence and severity of lesions was recorded for 19 days after viral inoculation. Infection rates, peak lesion scores, peak virus titers, areas under virus titer-day curves, and lesion score-day curves between PBS placebo-treated and PEG drug-treated or AC placebo-treated and AC drug-treated animals were compared using the Mann-Whitney U rank sum test. A p-value of 0.05 or less was considered significant.

The effect of topical treatment with ACV preparations on vaginal viral replication is shown in Table I. Only treatment with the ACV-MP preparations (5% ACV-MP-PEG or 5% ACV-MP-AC) significantly reduced the virus titer-day area under the curve (AUC) and mean peak virus titers.

TABLE I

EFFECT OF TREATMENT WITH ACYCLOVIR MONOPHOSPHATE ON VAGINAL VIRUS TITERS OF GUINEA PIGS INOCULATED INTRAVAGINALLY WITH AN ACYCLOVIR RESISTANT HSV-2

| Treatment[A] | #Virus Positive/# Inoculated | Virus Titer-Day Area Under Curve | P-Value | Mean Peak Virus Titer | P-Value |
|---|---|---|---|---|---|
| Placebo-PBS | 10/10 | 31.6 | — | 5.0 | — |
| Placebo-AC | 10/10 | 34.6 | NS[B] | 5.1 | NS |
| ACV-PEG | 10/10 | 33.4 | NS | 5.2 | NS |
| ACV-AC | 10/10 | 27.9 | NS | 4.6 | NS |
| ACV-MP-PEG | 6/10 | 3.4 | <0.001 | 2.0 | <0.001 |
| ACV-MP-AC | 9/10 | 14.5 | 0.001 | 3.7 | <0.05 |

[A]Topical and intravaginal treatment was initiated 24 hours after viral inoculation and was continued three times daily for 7 days. Acyclovir content on a molar basis was lower in the tests conducted with acyclovir monophosphate (14.5 mmol/100 ml) versus those conducted with the neat acyclovir (22.2 mmol/100 ml).
[B]NS = Not Statistically Significant when compared to the appropriate placebo-treated group.

The effect of topical treatment with ACV preparations on lesion development is depicted in Table II. Both ACV and ACV-MP preparations significantly altered the lesion score-day AUC when compared to the appropriate placebo-treated group. However, only therapy with 5% ACV-MP-PEG significantly reduced mean peak lesion scores.

TABLE II

EFFECT OF TREATMENT WITH ACYCLOVIR MONOPHOSPHATE ON EXTERNAL LESION DEVELOPMENT IN AN ACYCLOVIR RESISTANT GENITAL HSV-2 INFECTION OF GUINEA PIGS

| Treatment[A] | Lesion Score-Day Area Under Curve | P-Value | Mean Peak Lesion Score | P-Value |
|---|---|---|---|---|
| Placebo-PBS | 28.3 | — | 3.0 | — |
| Placebo-AC | 34.2 | NS[B] | 3.5 | NS |
| ACV-PEG | 9.5 | 0.001 | 1.8 | NS |
| ACV-AC | 19.3 | 0.01 | 2.5 | NS |
| ACV-MP-PEG | 1.7 | <0.001 | 0.7 | <0.001 |
| ACV-MP-AC | 23.4 | <0.05 | 2.3 | NS |

[A]Topical and intravaginal treatment was initiated 24 hours after viral inoculation and was continued three times daily for 7 days. Acyclovir content on a molar basis was lower in the tests conducted with acyclovir monophosphate (14.5 mmol/100 ml) versus those conducted with the neat acyclovir (22.2 mmol/100 ml).
[B]NS = Not Statistically Significant when compared to the appropriate placebo-treated group.

In the guinea pig model of an ACV-resistant HSV-2 genital herpes infection, only ACV-MP significantly reduced vaginal viral replication. Also, the ACV-MP-PEG treated group had the lowest virus titer-day and mean peak titer values. While both ACV-MP and ACV altered lesion development, the drugs in PEG had lower scores than those in AC. Additionally, animals receiving ACV-MP-PEG had the lowest lesion score-day and mean peak lesion scores.

Moreover, throughout the study, there were no signs of any irritation of the genital area or any other toxicity in uninfected ACV preparation-treated animals.

These results demonstrate the strong activity of acyclovir monophosphate in treating HSV-2 genital herpes. Further, it is interesting to note that polyethylene glycol dispersed acyclovir monophosphate showed the best efficacy in treating lesions.

EXAMPLE XII

Activity Of Acyclovir Diphosphate

The procedure of Example 8 is repeated using a formulation having only acyclovir diphosphate (ACV-DP) as the acyclovir derivative. Efficacy superior to that of ACV alone is observed.

EXAMPLE XIII

Activity Of Acyclovir Monophosphate Glycerol

The procedure of Example 8 is repeated using a formulation having only acyclovir monophosphate glycerol (ACV-MP-G) as the acyclovir derivative. Efficacy superior to that of ACV alone is observed.

EXAMPLE XIV

Activity Of Acyclovir Diphosphate Glycerol

The procedure of Example 8 is repeated using a formulation having only acyclovir diphosphate glycerol (ACV-DP-glycerol) as the acyclovir derivative. Efficacy superior to that of ACV alone is observed.

EXAMPLE XV

Activity Of Acyclovir Monophosphate Morpholidate

The procedure of Example 8 is repeated using a formulation having only acyclovir monophosphate morpholidate (ACV-MP-morpholidate) as the acyclovir derivative. Efficacy superior to that of ACV alone is observed.

EXAMPLE XVI

Activity Of Acvclovir Monophosphate Isopropylidene Glycerol

The procedure of Example 8 is repeated using a formulation having only acyclovir monophosphate isopropylidene glycerol (ACV-MP-isoP-G) as the acyclovir derivative. Efficacy superior to that of ACV alone is observed.

EXAMPLE XVII

Activity Of Acyclovir Diphosphate Isopropylidene Glycerol

The procedure of Example 8 is repeated using a formulation having only acyclovir diphosphate isopropylidene glycerol (ACV-DP-isoP-G) as the acyclovir derivative. Efficacy superior to that of ACV alone is observed.

EXAMPLE XVIII

Solubility Of Acyclovir Monophosphate And Salts

Various salts of acyclovir monophosphate were tested for solubility as follows:

Two ml of distilled water was placed in each of three 10 ml beakers, each beaker having magnetic stirring bars. In each individual flask, an acyclovir monophosphate salt, selected from potassium, sodium, sodium/ammonium, and $H^+$(free acid), was added until a saturated solution was formed. Each saturated salt solution was gravity filtered. The acyclovir monophosphate sodium/ammonium and free acid salt solutions were filtered through Whatman No. 4 filter paper and gave clear solutions. The potassium and sodium salt solutions were filtered through Whatman No. 1 filter paper and each gave slightly opalescent solutions.

One ml of each of the saturated salt solutions were transferred by pipette to preweighed round bottom flasks, and the solutions were allowed to dry. After all of the liquid had evaporated, the round bottom flasks were reweighed and the number of milligrams of acyclovir monophosphate salt present per milliliter was easily found.

The following Table sets forth the solubility of the various salts prepared as described above relative to acyclovir:

TABLE III

| Salt | Solubility as Compared to Acyclovir |
|---|---|
| $H^+$ | 21 X |
| $K^+$ | 85 X |
| $Na^+/NH_4^+$ | 100 X |
| $Na^+$ | 108 X |

It will be appreciated in view of the results shown in Table III, that through formation of a salt of the acyclovir monophosphate, solubility can be dramatically enhanced. It is expected that other nucleoside monophosphates will exhibit similarly enhanced solubility. In this manner, it is possible to formulate topical compositions containing large quantities of acyclovir monophosphate because of the enhanced solubility of the salts.

There will be various modifications, improvements, and applications of the disclosed invention that will be apparent to those skilled in the art, and the present application is intended to cover such embodiments. Although the present invention has been described in the context of certain preferred embodiments, it is intended that the full scope of the disclosure be measured only by reference to the following claims.

What is claimed is:

1. A method for treatment of a mammal infected with an acyclovir-resistant strain of herpes virus comprising administering to said mammal an effective amount of acyclovir phosphate.

2. A method for treatment of a mammal infected with herpes simplex virus, type I (HSV-I), comprising administering to said mammal an effective amount of acyclovir phosphate.

3. A method for treatment of an acyclovir-resistant herpes virus infection of a mammalian cell comprising administering an effective amount of acyclovir phosphate intracellularly by contacting said cell with an effective amount of acyclovir phosphate.

4. A method for treatment of a herpes simplex virus, type I (HSV-I), infection of a cell comprising administering an effective amount of acyclovir phosphate intracellularly by contacting said cell with an effective amount of acyclovir phosphate.

5. A method for treatment of a mammal infected with an acyclovir-resistant strain of herpes virus by delivering an effective amount of acyclovir phosphate through a biological membrane and into the cytoplasm of a herpes virus infected cell of said mammal comprising contacting the surface of said cell with an effective amount of acyclovir phosphate.

6. A method for treatment of a mammal infected with herpes simplex virus, type I (HSV-I), by delivering an effective amount of acyclovir phosphate through a biological membrane and into the cytoplasm of a herpes virus infected cell of said mammal comprising contacting the surface of said cell with an effective amount of acyclovir phosphate.

7. A method according to any one of claims 1–6 wherein the infected mammal is a human being.

8. A method according to any one of claims 2, 4, or 6 wherein the herpes virus infected cells are in the cutaneous or mucosal tissues of the mammal.

9. A method according to any one of claims 2, 4 or 6 wherein the herpes virus infection is in the orofacial region of the body of the mammal.

10. A method according to any one of claims 1, 3 or 5 wherein the acyclovir resistance of the virus is due to an alteration in the viral gene coding for thymidine kinase.

* * * * *